United States Patent
Taeschler et al.

(10) Patent No.: US 9,771,367 B2
(45) Date of Patent: Sep. 26, 2017

(54) METHOD FOR PREPARATION OF ALKYLATED OR FLUORO, CHLORO AND FLUOROCHLORO ALKYLATED COMPOUNDS BY HETEROGENEOUS CATALYSIS

(71) Applicant: Lonza Ltd, Visp (CH)

(72) Inventors: Christoph Taeschler, Visp (CH); Matthias Beller, Nienhagen (DE); Helfried Neumann, Rostock (DE); Lin He, Rostock (DE); Kishore Natte, Rostock (DE); Stefan Ellinger, Visp (CH); Florencio Zaragoza Doerwald, Visp (CH)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 15/310,295

(22) PCT Filed: Jun. 4, 2015

(86) PCT No.: PCT/EP2015/062474
§ 371 (c)(1),
(2) Date: Nov. 10, 2016

(87) PCT Pub. No.: WO2015/185677
PCT Pub. Date: Dec. 10, 2015

(65) Prior Publication Data
US 2017/0158695 A1     Jun. 8, 2017

Related U.S. Application Data

(60) Provisional application No. 62/008,830, filed on Jun. 6, 2014.

(30) Foreign Application Priority Data

| Jun. 6, 2014 | (EP) | 14171598 |
| Nov. 3, 2014 | (EP) | 14191394 |
| Nov. 7, 2014 | (EP) | 14192286 |
| Feb. 27, 2015 | (EP) | 15156931 |

(51) Int. Cl.
| C07B 37/04 | (2006.01) |
| C07D 473/12 | (2006.01) |
| C07D 207/323 | (2006.01) |
| C07D 333/12 | (2006.01) |
| C07D 333/28 | (2006.01) |
| C07D 213/127 | (2006.01) |
| C07D 213/26 | (2006.01) |
| C07C 17/32 | (2006.01) |
| C07C 22/08 | (2006.01) |

(52) U.S. Cl.
CPC ............ *C07D 473/12* (2013.01); *C07B 37/04* (2013.01); *C07C 17/32* (2013.01); *C07C 22/08* (2013.01); *C07D 207/323* (2013.01); *C07D 213/127* (2013.01); *C07D 213/26* (2013.01); *C07D 333/12* (2013.01); *C07D 333/28* (2013.01)

(58) Field of Classification Search
CPC ...................................................... C07B 37/04
See application file for complete search history.

(56) References Cited

U.S. PATENT DOCUMENTS

| 6,096,926 A | 8/2000 | Roques et al. |
| 6,203,721 B1 | 3/2001 | Roques et al. |
| 6,355,849 B1 | 3/2002 | Roques et al. |

FOREIGN PATENT DOCUMENTS

| EP | 0114359 | 8/1984 |
| EP | 1947092 | 7/2008 |
| JP | S57142923 A | 1/1983 |
| JP | S6226241 A | 2/1987 |
| JP | 2000500480 A | 1/2000 |
| JP | H07504414 | 1/2000 |
| JP | 200106593 A | 5/2001 |
| JP | 2007153876 A | 6/2007 |
| JP | 2008137992 A | 6/2008 |
| WO | WO 93/16969 | 9/1993 |

OTHER PUBLICATIONS

Lin He et.al., "Heterogeneous Platinum-Catalyzed C-H Perfluoroalkylation of Arenes and Heteroarenes", Angewandte Chemie International Edition, vol. 54, No. 14, Feb. 10, 2015, pp. 4320-4324.
Rebecca N. Loy et al., "Palladium-Catalyzed C-H Perfluoroalkylation of Arenes", Organic Letters, vol. 13, No. 10, May 20, 2011, pp. 2548-2551.
International Search Report and Written Opinion for PCT/EP2015/062474, Dated Jul. 28, 2015.
International Preliminary Report on Patentability for PCT/EP2015/062474, Dated Oct. 21, 2015.

*Primary Examiner* — Shawquia Jackson
(74) *Attorney, Agent, or Firm* — Dority & Manning, PA

(57) ABSTRACT

The invention discloses a method for preparation of alkylated or fluoro, chloro and fluorochloro alkylated compounds by a heterogeneous Pt/C-catalyzed alkylation or fluoro, chloro and fluorochloro alkylation with alkyl halides or with fluoro, chloro and fluorochloro alkyl halides in the presence of $Cs_2CO_3$ or $CsHCO_3$.

16 Claims, No Drawings

METHOD FOR PREPARATION OF ALKYLATED OR FLUORO, CHLORO AND FLUOROCHLORO ALKYLATED COMPOUNDS BY HETEROGENEOUS CATALYSIS

RELATED APPLICATIONS

This application is the national stage entry of International Patent Application No. PCT/EP2015/062474 having a filing date of Jun. 4, 2015, which claims the filing benefit of European Patent Application No. 14171598.7, having a filing date of Jun. 6, 2014, U.S. Provisional Patent Application No. 62/008,830, having a filing date of Jun. 6, 2014, European Patent Application No. 14191394.7, having a filing date of Nov. 3, 2014, European Patent Application No. 14192286.4, having a filing date of Nov. 7, 2014, and European Patent Application No. 1515931.6, having a filing date of Feb. 27, 2015, all of which are incorporated herein by reference in their entirety.

The invention discloses a method for preparation of alkylated or fluoro, chloro and fluorochloro alkylated compounds by a heterogeneous Pt/C-catalyzed alkylation or fluoro, chloro and fluorochloro alkylation with alkyl halides or with fluoro, chloro and fluorochloro alkyl halides in the presence of $Cs_2CO_3$ or $CsHCO_3$.

BACKGROUND OF THE INVENTION

Organofluorine chemistry plays an importance role in medicinal, agricultural, and material sciences and fields. Fluoroalkyl groups have strong effects such as high stability and lipophilicity, in addition, longer fluoroalkyl groups have high water-, oil-resistance and low friction.

Homogeneous catalysis still suffers from the inherent problems associated with homogeneous catalyzed reactions due to the use of unrecoverable metals and ligands, as well as inconveniences with regard to catalyst handling, recyclability, and separation of the catalyst from products, impede the transfer of these advances to large-scale industrial processes. Furthermore expensive and structurally complicated ligands are required in homogeneous catalysis, which are often not even commmercially available for use on industrial scale.

EP 0 114 359 A1 discloses a process for the manufacture of perfluoralkyl substituted carbocyclic or heterocyclic compounds by reaction of perfluoroalkyl iodides with unsubstituted or substituted carbocyclic or heterocyclic compounds at elevated temperatures and in presence of at least one alkaline salt, characterized by carrying out the reaction in the presence of at least one metal of the first or eight auxiliary group of the periodic table or in the presence of a complex compound containing said metal as the central atom.

The examples show the use of $K_2CO_3$ as base and reaction temperatures of 150° C., 160° C. and 170° C. for the heterogeneously catalyzed reactions. For the preparation of $C_8F_{17}$—$C_6H_5$ in Example 1 using a Ru/C catalyst a yield of 89.2% is disclosed.

In case of Pt/C in examples 5 to 7 a yield of 55 to 76 mol % is disclosed for the conversion of benzene with three different perfluoroalkyl iodides.

WO 93/16969 A discloses a process for the catalytic perfluoroalkylation of aromatic compounds, wherein a perfluoroalkyl iodide or mixture of iodides is reacted with an aromatic compound in the presence of an aqueous base, such as an alkali metal hydroxide or carbonate, and discloses that further improvements in rate and yield are secured by employing, as the catalyst, a noble metal supported on porous silica microspheres.

The examples show the use of $K_2CO_3$ and KOH as bases and reaction temperature of 170° C., 180° C. and 200° C.

Example 1 reports a yield of 93% using a catalyst consisting of 2% Pd and 0.1% Pt on a silica support.

The use of a support different from silica is reported in example 2, 17 and 18, example 2 discloses a yield of only 55% using 5% Ru/C as catalyst, example 17 and 18 disclose a yield of only 4.5% and 2.5% respectively using 2% Pd/C as catalyst.

Example 19 and 20 disclose the use of 5% Pd and 1% cobalt respectively on high surface area carbon (surface area 2000 $m^2$/gram) and a yield of 87% and 88% respectively.

A special procedure for the preparation of the silica supported catalyst is disclosed.

EP 1 947 092 A1 discloses perfluoroalkylation of nucleobases with a perfluoroalkyl halide in the presence of a sulfoxide, a peroxide and an iron compound. A specifically mentioned catalytic system is a $Fe_2(SO_4)_3/H_2SO_4/H_2O_2$ system.

There was a need for a heterogeneously catalyzed process for the preparation of perfluoroalkylated compounds, which provides high yields, which does not require high temperatures and does not require the use of catalysts prepared according to special procedures. The method should be applicable to a wide variety of substrates and should be compatible with a wide variety of functional groups. Furthermore the method should not be restricted to iodides as alkylating agent only, but should also work with other halides. And the method should work not only with perfluorinated alkyl iodides, but also with fluorinated and chlorinated alkyl halides.

Unexpectedly the use of $Cs_2CO_3$ or $CsHCO_3$ as base together with Pt/C as catalyst meets these requirements. No dialkylated products are observed. The reaction does not mandatorily require inert atmosphere but can even be done under air atmosphere. The catalyst can be reused and is not deactivated by the reaction.

Compared to prior art, various advantages are observed as outlined in the examples below, e.g. in case of naphtalene not only the yield is higher but also the selectivity is better, only the alpha position is substituted. The method is applicable both to aromatic and non-aromatic compounds. Also heteroaromatic compounds can be converted, even nonactivated thiophenes react smoothly at comparably low temperatures, n-methyl pyrrole reacts under mild conditions at 50° C. Also the notoriously difficult pyridines, which are very stable to many alkylating reagents and even can be used as a solvent in some perfluoroalkylation reactions, were converted with high yields. Also with caffeine high yields are obtained.

In this text, the following meanings are used, if not otherwise stated:
alkyl linear or branched alkyl;
DBU 1,8-diazabicyclo[5.4.0]undec-7-en
halide $F^-$, $Cl^-$, $Br^-$ or $I^-$, preferably $Cl^-$, $Br^-$, and $I^-$, more preferably $Br^-$ and $I^-$;
halogen F, Cl, Br or I; preferably F, Cl or Br; more preferably F or Cl;
HRMS EI: High Resolution Mass Spectrometry Electron Impact
"linear" and "n-" are used synonymously with respect to the respective isomers of alkanes;
MTBE methyl tert-butyl ether;

Pt/C platinum on charcoal
RT room temperature, it is used synonymously with the expression ambient temperature;
THF tetrahydrofurane
"wt %", "% by weight" and "weight-%" are used synonymously and mean percent by weight.

SUMMARY OF THE INVENTION

Subject of the invention is a method for the preparation of a alkylated or a fluoro, chloro or fluorochloro alkylated compound by a reaction of a compound COMPSUBST with a compound FCLALKYLHALIDE with heterogeneous catalysis using a catalyst CAT in the presence of a compound CAESCARB;
FCLALKYLHALIDE is a compound of formula (III);

R3-X    (III)

X is Cl, Br or I;
R3 is $C_{1-20}$ alkyl or a $C_{1-20}$ alkyl wherein in the alkyl chain at least one hydrogen is substituted by F or Cl;
CAESCARB is $Cs_2CO_3$, $CsHCO_3$ or a mixture thereof;
CAT is Pt/C;
COMPSUBST is selected from the group consisting of a compound COMPSUBST-I, compound of formula (II), compound of formula (IV), polystyrene, ethene and ethine;
  the ethene being unsubstituted or substituted by 1, 2 or 3 substitutents selected from the group consisting of $C_{1-10}$ alkyl, $C_{3-8}$ cycloalkyl, $C_{1-4}$ alkoxy, N(R10)R11, CN, NO, $NO_2$, F, Cl, Br, I, $CF_3$, $(CH_2)_m$—C(O)Y1, $S(O)_2R50$, CH═C(H)R28,

C≡C—R24, benzyl, phenyl and naphthyl;
  the ethine being unsubstituted or substituted by 1 substitutent selected from the group consisting of $C_{1-10}$ alkyl, $C_{3-8}$ cycloalkyl, $C_{1-4}$ alkoxy, N(R10)R11, CN, NO, $NO_2$, F, Cl, Br, I, $CF_3$, $(CH_2)_m$—C(O)Y1, $S(O)_2R50$, CH═C(H)R28,

C≡C—R24, benzyl, phenyl and naphthyl;

(II)

R40, R41
 \ /
  X
 / \
H   H (IV)

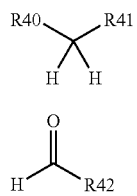

R40 and R41 are identical or different and independently from each other selected from the group consisting of $(CH_2)_q$—C(O)R13 and CN;
R42 is selected from the group consisting of $(CH_2)_q$—C(O)R13, CN, R13;
COMPSUBST-I contains a ring RINGA;

RINGA is a 5 or 6 membered carbocyclic or heterocyclic ring,
  when RINGA is a heterocyclic ring, then RINGA has 1, 2 or 3 identical or different endocyclic heteroatoms independently from each other selected from the group consisting of N, O and S,
  when RINGA is a 5 membered ring, then RINGA is unsubstituted or substituted by 1, 2, 3 or 4 identical or different substitutents,
  when RINGA is a 6 membered ring then RINGA is unsubstituted or substituted by 1, 2, 3, 4 or 5 identical or different substitutents,
  any of said substitutents of RINGA is independently from any other of said substitutent of RINGA selected from the group consisting of $C_{1-10}$ alkyl, $C_{3-8}$ cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, $S(O)_2R50$, CH═C(H)R28,

C≡C—R24, benzyl, phenyl and naphthyl;
RINGA can be condensed with a ring RINGB, RINGB is a 5 or 6 membered carbocyclic or heterocyclic ring,
  when RINGB is a heterocyclic ring, is contains 1, 2 or 3 identical or different endocyclic heteroatoms independently from each other selected from the group consisting of N, O and S;
RINGB is unsubstituted or substituted with 1, 2 or 3 in case of RINGB being a 5 membered ring, with 1, 2, 3 or 4 in case of RINGB being a 6 membered ring, identical or different substitutents independently from each other selected from the group consisting of $C_{1-10}$ alkyl, $C_{3-8}$ cycloalkyl, $C_{1-4}$ alkoxy, OH, N(R17)R18, CN, NH—OH, NO, $NO_2$, F, Cl, Br, I, $CF_3$, $(CH_2)_n$—C(O)Y2, $S(O)_2R51$, CH═C(H)R38,

C≡C—R34, benzyl, phenyl and naphthyl;
  any of said $C_{1-10}$ alkyl substitutent of RINGA or RINGB is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;
  any of said benzyl, phenyl and naphthyl substitutent of RINGA or RINGB is independently from each other unsubstituted or substituted with 1, 2, 3, 4 or 5 identical or different substitutents selected from the group consisting of halogen, $C_{1-4}$ alkoxy, $NO_2$ and CN;
m, n and q are identical or different and independently from each other 0, 1, 2, 3, 4, 5, 6, 7, 8, 9 or 10;
Y1, Y2 and R13 are identical or different and independently from each other selected from the group consisting of H, OH, C(R14)(R15)R16, $C_{1-6}$ alkyl, O—$C_{1-6}$ alkyl, phenyl, benzyl, O-phenyl, O—$C_{1-6}$ alkylen-O—$C_{1-6}$ alkyl and N(R19)R20;
R14, R15 and R16 are identical or different and independently from each other selected from the group consisting of H, F, Cl and Br;

R10, R11, R17, R18, R19 and R20 are identical or different and are independently from each other H or $C_{1-6}$ alkyl, or R10 and R11, R17 and R18 or R19 and R20 represent together a tetramethylene or a pentamethylene chain;

R50 and R51 are identical or different and independently from each other selected from the group consisting of OH, $C_{1-6}$ alkyl and $C_{1-6}$ alkoxy;

R24, R34, R28 and R38 are identical or different and independently from each other selected from the group consisting of H, $C_{1-10}$ alkyl, C(R25)(R26)-O—R27;

R25, R26 and R27 are identical or different and independently from each other selected from the group consisting of H and $C_{1-10}$ alkyl.

DETAILED DESCRIPTION OF THE INVENTION

Preferably, COMPSUBST is selected from the group consisting of compound COMPSUBST-I, compound of formula (II), compound of formula (IV), polystyrene, ethene and ethine;
the ethene being unsubstituted or substituted by 1 or 2 substitutents selected from the group consisting of $C_{1-10}$ alkyl, $C_{3-6}$ cycloalkyl, $C_{1-4}$ alkoxy, N(R10)R11, CN, F, Cl, Br, I, $CF_3$, $(CH_2)_m$—C(O)Y1, $S(O)_2R50$, benzyl, phenyl and naphthyl;
the ethine being unsubstituted or substituted by 1 substitutent selected from the group consisting of $C_{1-10}$ alkyl, $C_{3-6}$ cycloalkyl, $C_{1-4}$ alkoxy, N(R10)R11, CN, F, Cl, Br, I, $CF_3$, $(CH_2)_m$—C(O)Y1, $S(O)_2R50$, benzyl, phenyl and naphthyl;
with COMPSUBST-I being selected from the group consisting of

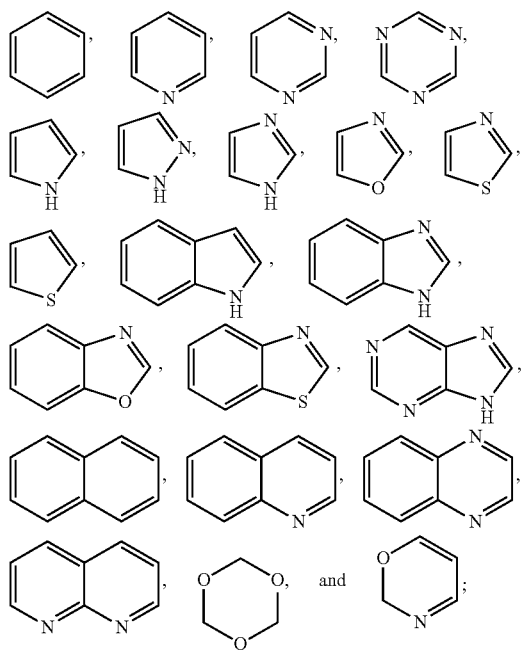

with COMPSUBST-I being unsubstituted or substituted
by 1, 2, 3 or 4 in case of COMPSUBST-I being a monocyclic compound with 5 endocyclic atoms,
by 1, 2, 3, 4 or 5 in case of COMPSUBST-I being a monocyclic compound with 6 endocyclic atoms,
by 1, 2, 3, 4, 5 or 6 in case of COMPSUBST-I being a bicyclic compound wherein a 5-membered and a 6-membered ring are ortho-fused,
by 1, 2, 3, 4, 5, 6 or 7 in case of COMPSUBST-I being a bicyclic compound wherein two 6-membered rings are ortho-fused,
preferably, COMPSUBST I is unsubstituted or substituted by 1, 2, 3, 4 or 5,
identical or different substituents independently from each other selected from the group consisting of $C_{1-10}$ alkyl, $C_{3-8}$ cycloalkyl, $C_{1-4}$ alkoxy, OH, C(H)=O, N(R10)R11, CN, NH—OH, NO, $NO_2$, F, Cl, Br, I, $CF_3$, $(CH_2)_m$—C(O)Y1, $S(O)_2R50$, CH=C(H)R28,

C≡C—R24, benzyl, phenyl and naphthyl;
said $C_{1-10}$ alkyl substitutent of COMPSUBST-I is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;
said benzyl, phenyl and naphthyl substitutent of COMPSUBST-I is independently from each other unsubstituted or substituted with 1, 2, 3, 4 or 5 identical or different substituents selected from the group consisting of halogen, $C_{1-4}$ alkoxy, $NO_2$ and CN;
compound of formula (II), compound of formula (IV), R10, R11, m, n, Y1, Y2, R28, R50 and R24 are defined as above, also with all their embodiments.

Preferably, m, n and q are identical or different and independently from each other 0, 1, 2, 3 or 4;
more preferably, m, n and q are 0 or 4.

In another embodiment, Y1, Y2 and R13 are identical or different and independently from each other selected from the group consisting of H, OH, C(R14)(R15)R16, $C_{2-6}$ alkyl, O—$C_{1-6}$ alkyl, phenyl, benzyl, O-phenyl, O—$C_{1-6}$ alkylen-O—$C_{1-6}$ alkyl and N(R19)R20.

Preferably, Y1, Y2 and R13 are identical or different and independently from each other selected from the group consisting of H, OH, $C_{1-2}$ alkyl, and O—$C_{1-2}$ alkyl.

More preferably, COMPSUBST-I is unsubstituted or substituted
by 1, 2 or 3 in case of COMPSUBST-I being a monocyclic compound with 5 endocyclic atoms,
by 1, 2, 3, 4 or 5 in case of COMPSUBST-I being a monocyclic compound with 6 endocyclic atoms,
by 1, 2, 3, 4 or 5 in case of COMPSUBST-I being a bicyclic compound wherein a 5-membered and a 6-membered ring are ortho-fused,
by 1, 2, 3 or 4 in case of COMPSUBST-I being a bicyclic compound wherein two 6-membered rings are ortho-fused,
identical or different substituents independently from each other selected from the group consisting of $C_{1-4}$ alkyl, $C_{1-4}$ alkoxy, OH, C(H)=O, N(R10)R11, CN, F, Cl, Br, $CF_3$, $(CH_2)_m$—C(O)Y1, and $S(O)_2R50$;
said $C_{1-4}$ alkyl substitutent of COMPSUBST-I is unsubstituted or substituted with 1, 2 or 3 identical or different substituents selected from the group consisting of halogen;
with R10, R11, Y1 and R50 as defined above, also with all their embodiments.

Especially, COMPSUBST is selected from the group consisting of benzene, pyrazole,
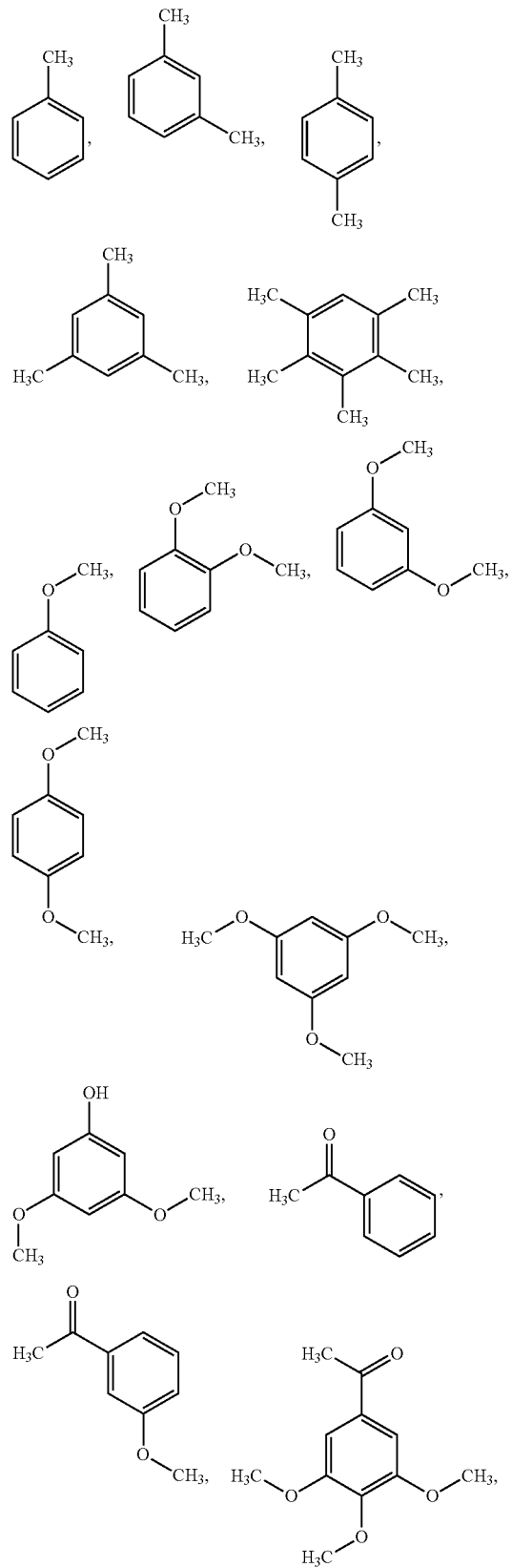
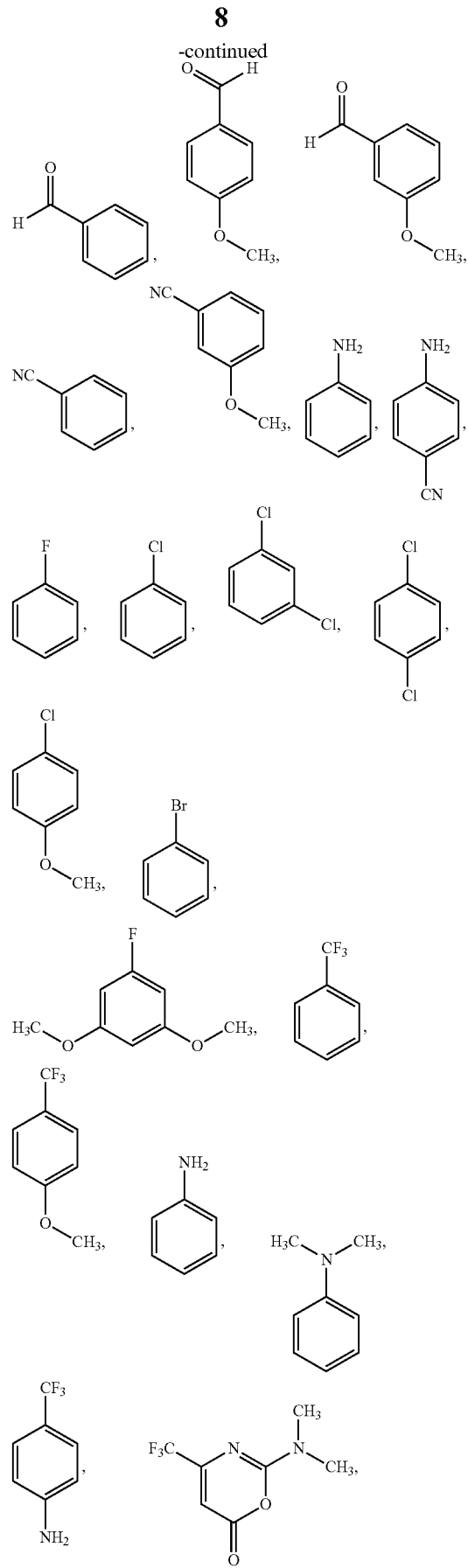

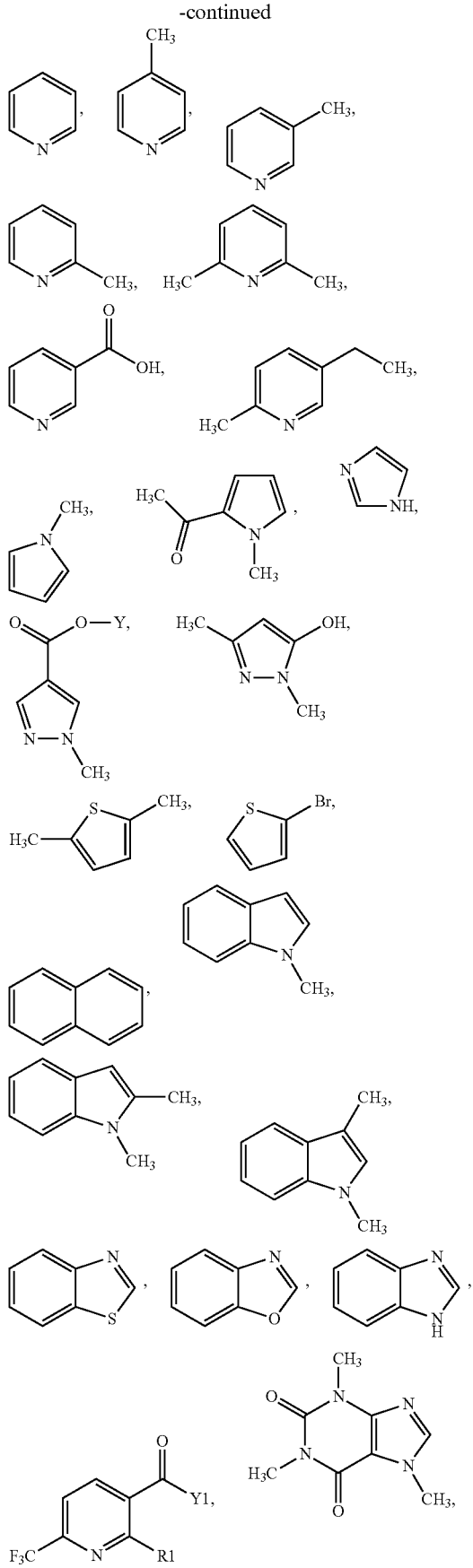

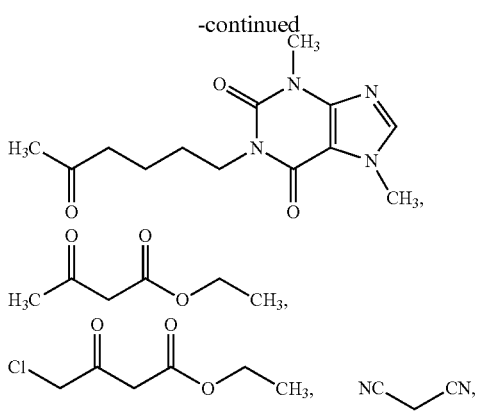

compound of formula (V), compound of formula (VI), polystyrene, ethene and ethine;

Y is $C_{1-6}$ alkyl;

the ethene being unsubstituted or substituted by 1 or 2 substitutents selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl and phenyl;

the ethine being unsubstituted or substituted by 1 substitutent selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl and phenyl;

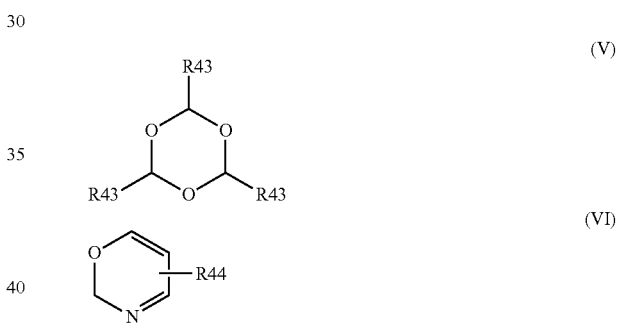

wherein

R43 is H or $CH_3$;

R44 is selected from the group consisting of $C_{1-10}$ alkyl, $C_{1-4}$ alkoxy, OH, N(R10)R11, CN, NO, $NO_2$, F, Cl, Br, I, $CF_3$, $(CH_2)_m$—C(O)Y1, $S(O)_2R50$;

with R10, R11, m, Y1 and R50 as defined above, also with all their embodiments.

Embodiments of the substituted ethene are propene, ethene-1,1-diyldibenzene and 3,3-dimethylbut-1-ene.

An embodiment of the substituted ethine is 1-octyne.

Preferably, Y is methyl or ethyl.

An embodiment of COMPSUBST is

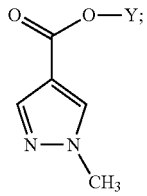

Y is methyl or ethyl, preferably ethyl.

The alkylated or fluoro, chloro or fluorochloro alkylated compound is called compound ALKYLCOMPSUBST in the following.

Preferably, FCLALKYLHALIDE is a compound of formula (III);

$$R3-X \qquad (III)$$

X is Cl, Br or I;
R3 is $C_{1-20}$ alkyl or a $C_{1-20}$ alkyl, wherein any of the hydrogens is substituted by F or Cl; more preferably,
R3 is $C_{1-15}$ alkyl or $C_{1-15}$ alkyl, wherein any of the hydrogens is substituted by F or Cl; even more preferably,
R3 is $C_{1-10}$ alkyl or $C_{1-10}$ alkyl, wherein any of the hydrogens is substituted by F or Cl.

The expression "wherein any of the hydrogens is substituted by F or Cl" means, that at least one hydrogen in the alkyl chain is substituted by F or Cl, and any other hydrogen in the alkyl chain can independently from any other hydrogen in the alkyl chain also be substituted by F or Cl.

Therefore, preferably, FCLALKYLHALIDE is a compound of formula (III);

$$R3-X \qquad (III)$$

X is Cl, Br or I;
R3 is $C_{1-20}$ alkyl or a $C_{1-20}$ alkyl wherein in the alkyl chain at least one hydrogen is substituted by F or Cl;
more preferably,
R3 is $C_{1-15}$ alkyl or $C_{1-15}$ alkyl wherein in the alkyl chain at least one hydrogen is substituted by F or Cl;
even more preferably,
R3 is $C_{1-10}$ alkyl or $C_{1-10}$ alkyl wherein in the alkyl chain at least one hydrogen is substituted by F or Cl.
Preferably,
X is Br or I;
more preferably,
X is I;
also with R3 in all its embodiments.

In an especial ambodiment, compound FCLALKYL-HADLIDE is a perfluoroalkyl halide, $F_2HC$—Cl or $F_2HC$—Br, preferably FCLALKYLHADLIDE is a perfluoroalkylated bromide or iodide, $F_2HC$—Cl or $F_2HC$—Br;
preferably
X is Cl, Br or I, and
R3 is perfluoro $C_{1-20}$ alkyl; or
FCLALKYLHADLIDE is $F_2HC$—Cl or $F_2HC$—Br;
more preferably,
X is Br or I, and
R3 is perfluoro $C_{1-20}$ alkyl; or
FCLALKYLHADLIDE is $F_2HC$—Cl or $F_2HC$—Br;
even more preferably,
X is Br or I, and
R3 is perfluoro $C_{1-15}$ alkyl; or
FCLALKYLHADLIDE is $F_2HC$—Cl or $F_2HC$—Br.
In particular, FCLALKYLHALIDE is selected from the group consisting of $F_{21}C_{10}$—I, $F_{17}C_8$—I, $F_{13}C_6$—I, $F_9C_4$—I, $F_3C$—I, $F_3C$—Br, $F_3C$—Cl, $F_2HC$—Cl, and $F_2HC$—Br;
more in particular, FCLALKYLHALIDE is selected from the group consisting of n-$F_{21}C_{10}$—I, n-$F_{17}C_8$—I, n-$F_{13}C_6$—I, n-$F_9C_4$—I, $F_3C$—I, $F_3C$—Br, $F_3C$—Cl, $F_2HC$—Cl, and $F_2HC$—Br.

In one embodiment, the reaction is done in the presence of a compound COMPSALT;
COMPSALT is selected from the group consisting of NaI, KI, CsI and N(R30)(R31)(R32)R33I;
R30, R31, R32 and R33 are identical or different and independently from each other selected from the group consisting of H and $C_{1-10}$ alkyl;
preferably, R30, R31, R32 and R33 are identical or different and independently from each other selected from the group consisting of H and $C_{2-6}$ alkyl;
more preferably, COMPSALT is selected from the group consisting of NaI and (n-Bu)$_4$NI.

The reaction is preferably done in the presence of a compound COMPSALT and X is Cl or Br, preferably X is Cl.

CAT is Pt/C, that is CAT is platinum supported on carbon.
Preferably, CAT is Pt supported on charcoal, more preferably on activated charcoal.

Preferably, the amount of Pt in CAT is from 0.1 to 20%, more preferably from 0.5 to 15%, even more preferably from 1 to 12.5%, especially from 2 to 12.5%, the % are % by weight and are based on the combined weight of Pt and C in CAT.

Preferably, from 0.001 to 20%, more preferably from 0.01 to 15%, even more preferably from 0.025 to 12.5%, especially from 0.05 to 10%, of Pt are used in the reaction, the % are % by weight % and are based on the weight of FCLALKYLHALIDE.

Preferably, from 1 to 20 mol equivalents, more preferably 1 to 15 mol equivalents, even more preferably from 1 to 10 mol equivalents, of COMPSUBST are used in the reaction, the mol equivalents are based on the molar amount of FCLALKYLHALIDE.

Preferably, from 0.1 to 10 mol equivalents, more preferably 0.5 to 5 mol equivalents, even more preferably from 0.75 to 2.5 mol equivalents, of CAESCARB are used in the reaction, the mol equivalents are based on the molar amount of FCLALKYLHALIDE.

The reaction temperature of the reaction is preferably from 20 to 200° C., more preferably from 20 to 150° C., even more preferably from 30 to 140° C., especially from 30 to 130° C.

The reaction time of the reaction is preferably from 30 min to 48 h, more preferably from 1 h to 48 h, even more preferably from 2 h to 36 h.

Preferably, the reaction is done under inert atmosphere. Preferably, the inert atmosphere is achieved by the use if an inert gas preferably selected from the group consisting of argon, another noble gas, lower boiling alkane, nitrogen and mixtures thereof.

The lower boiling alkane is preferably a $C_{1-3}$ alkane, i.e. methane, ethane or propane.

The reaction can be done in a closed system, it can be done at a pressure caused by the chosen temperature in a closed system. It is also possible to apply pressure with said inert gas. It is also possible to carry out the reaction at ambient pressure.

The reaction can be done in a solvent SOL, SOL is preferably selected from the group consisting of alkanes, chlorinated alkanes, ketones, ethers, esters, aliphatic nitrils, aliphatic amides, sulfoxides, and mixtures thereof;
preferably SOL is selected from the group consisting of $C_{5-8}$ alkane, chlorinated $C_{5-8}$ alkane, acetone, methylethylketone, diethylketone, MTBE, tetrahydrofuran, methyltetrahydrofuran, ethylacetate, butylacetate, valeronitril, acetonitrile, dimethylformamide, dimethylacetamide, N-methylpyrrolidone, dimethylsulfoxide, and mixtures thereof.

It is also possible to use COMPSUBST simultaneously as substrate and as solvent.

As an alternative, the reaction can also be carried out in the absence of a solvent. In another embodiment, COMPSUBST is used as SOL.

The amount of SOL is preferably from 0.1 to 100 fold, more preferably from 1 to 50 fold, even more preferably from 1 to 25 fold, of the weight of FCLALKYLHALIDE.

After the reaction, ALKYLCOMPSUBST can be isolated by standard methods such as evaporation of volatile components, extraction, washing, drying, concentration, crystallization, chromatography and any combination thereof, which are known per se to the person skilled in the art.

COMPSUBST, CAESCARB, CAT and FCLALKYLHALIDE, are commercially available and can be prepared according to known procedures.

EXAMPLES

Yield:

The yield is given as a molar yield of the expected ALKYLCOMPSUBST based on molar amount of FCLALKYLHALIDE and was determined by quantitative GC analysis with hexadecane as internal standard, if not otherwise stated.

Conversion:

Conversion was determined by dection of the remaining FCLALKYLHALIDE by quantitative GC analysis with hexadecane as internal standard, if not otherwise stated.

Ratio of Isomers and Position of Alkylation were determined by NMR spectroscopy

Example 1

Perfluoralkylation of Benzene

A mixture of benzene (0.44 g, 5.6 mmol), n-$C_{10}F_{21}I$ (0.13 g, 0.2 mmol), Pt/C (Sigma-aldrich 330159, with 5 wt % Pt, the wt % are based on the combined weight of Pt and C, with ca. 50 wt % water, the wt % based on the combined amount of Pt, C and water, 78 mg, 0.01 mmol, 5 mol % Pt based on n-$C_{10}F_{21}I$), and $Cs_2CO_3$ (65 mg, 0.2 mmol) were placed in a magnetically stirred Wheaton vial, the Wheaton vial was placed in a well-plate in a Parr autoclave (Parr Instruments 4560 series). After replacing the air in the autoclave with nitrogen and increasing the pressure to 10 bars with nitrogen, the reaction mixture was stirred at 100° C. for 20 h. Then the reaction mixture was cooled, and then the pressure was released from the autoclave. After the addition of 25 ml dichloromethane the solids were removed by filtration. The filtrate showed a yield of 96%. Conversion of the n-$C_{10}F_{21}I$ was 100%. The filtrate was then extracted with water, concentrated, dissolved in a minimal amount of benzene and purified by pipette column chromatography using FluoroFlash® reverse phase silica gel (eluting with a gradient of 4:1 MeOH:$H_2O$ (10 mL), then MeOH (10 mL), then acetone (10 mL). The methanol fraction and the aceton fraction were collected, dried with $MgSO_4$, filtered and concentrated under vacuum to give 107 mg product with a content of 99 wt % of compound of formula (1)

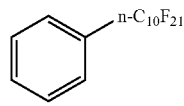
(1)

according to quantitative GC analysis. The identity of the product was confirmed using HRMS EI (m/z): [M]+ calculated for $C_{16}H_5F_{21}$; 596.00504. found: 596.00502.

Example 2

Trifluormethylation of Benzene

Step (a) Preparation of $CF_3Br$ Stock Solution

A stock solution of $CF_3Br$ in benzene was prepared by bubbling $CF_3Br$ into a 5 mL benzene. The solution was weighed before and after the $CF_3Br$ was added to measure the amount of $CF_3Br$ in the $CF_3Br$ stock solution.

Step (b) Reaction $CF_3Br$ stock solution (0.5 mL, 0.2 mmol, prepared according to step (a)), Pt/C (Sigma-aldrich 330159, with 5 wt % Pt, the wt % are based on the combined weight of Pt and C, with ca. 50 wt % water, the wt % based on the combined amount of Pt, C and water, 78 mg, 0.01 mmol, 5 mol % Pt based on $CF_3Br$), and $Cs_2CO_3$ (65 mg, 0.2 mmol) were placed in a magnetically stirred Wheaton vial, the Wheaton vial was placed in a well-plate in a Parr autoclave (Parr Instruments 4560 series). After replacing the air in the autoclave with nitrogen and increasing the pressure to 15 bars with nitrogen, the reaction mixture was stirred at 100° C. for 20 h. Then the reaction mixture was cooled, and then the pressure was released from the autoclave, and the solids were removed by filtration. The crude reaction mixture was analyzed by $^{19}$F-NMR using as internal standard 1,4-difluorobenzene showing an yield of 21% of trifluormethyl benzene.

Example 3

Perfluoroalkylation of Polystyrene

A mixture of polystyrene (0.10 g, corresponding to 1 mmol styrene), n-$C_{10}F_{21}I$ (0.13 g, 0.2 mmol), THF (1 mL), Pt/C (Sigma-aldrich 330159 with 5 wt % Pt, the wt % are based on the combined weight of Pt and C, with ca. 50 wt % water, the wt % based on the combined amount of Pt, C and water, 78 mg, 0.01 mmol, 5 mol % Pt based on n-$C_{10}F_{21}I$), and $Cs2CO3$ (65 mg, 0.2 mmol) were placed in a magnetically stirred Wheaton vial, the Wheatopn vial was placed in a well-plate in a Parr autoclave (Parr Instruments 4560 series). After replacing the air in the autoclave with nitrogen and increasing the pressure to 10 bars with nitrogen, the reaction mixture was stirred at 80° C. for 20 h. Then the reaction mixture was cooled, and then the pressure was released from the autoclave, and the solids were removed by filtration. Analysis of the product by $^{19}$F-NMR using as internal standard 1,4-difluorobenzene showed a yield of 95% based on the consumption of $C_{10}F_{21}I$ and a perfluoroalkylation of the polystyrene. Perfluoroalkylation ratio is ca. 20%, measured by $^{19}$F NMR using as internal standard 1,4-diflourobenzene.

Examples 4, 5 and 6

Example 1 was repeated with the differences given in table 1.

TABLE 1

| Example | T [° C.] | t [h] | Conversion [%] | Yield [%] |
|---|---|---|---|---|
| 4 | 80 | 36 | 95 | 92 |
| 5 | 80 | 36 | 91 | 90 |
| 6 | 80 | 36 | 87 | 84 |

Further differences were:

Example 5 was not inertized and was stirred under atmospheric pressure and under air atmosphere.

Example 6 shows the results of the third run of CAT.

Comparative Examples 1 to 14

Comparative examples 1 to 14 were done according to example 1 with the conditions and any differences given in table 2.

TABLE 2

| Comparative example | Catalyst | Bases | T [° C.] | t [h] | Conversion [%] | Yield [%] |
|---|---|---|---|---|---|---|
| 1 | Pd/C | $Cs_2CO_3$ | 100 | 20 | 63 | 61 |
| 2 | Ru/C | $Cs_2CO_3$ | 100 | 20 | 27 | 24 |
| 3 | $Ru/Al_2O_3$ | $Cs_2CO_3$ | 100 | 20 | 25 | 21 |
| 4 | Rh/C | $Cs_2CO_3$ | 100 | 20 | 41 | 39 |
| 5 | $Pt/TiO_2$ | $Cs_2CO_3$ | 100 | 20 | 46 | 45 |
| 6 | $Pt/Al_2O_3$ | $Cs_2CO_3$ | 100 | 20 | 79 | 77 |
| 7 | $Pt/ZrO_2$ | $Cs_2CO_3$ | 100 | 20 | 62 | 61 |
| 8 | $Pt/CeO_2$ | $Cs_2CO_3$ | 100 | 20 | 51 | 49 |
| 9 | Pt/C | DBU | 100 | 8 | 100 | 56 |
| 10 | Pt/C | $K_3PO_4$ | 100 | 20 | 67 | 60 |
| 11 | Pt/C | $K_2CO_3$ | 100 | 20 | 54 | 49 |
| 12 | Pt/C | $NEt_3$ | 100 | 20 | 74 | 51 |
| 13 | $PtCl_2$ | $Cs_2CO_3$ | 80 | 36 | 19 | 18 |
| 14 | $PtI_2$ | $Cs_2CO_3$ | 80 | 36 | 15 | 14 |

The comparative examples, when compared with the inventive examples, show that the combination Pt/C with $Cs_2CO_3$ according to instant invention gives superior results, the catalysts different from Pt/C or bases different from $Cs_2CO_3$ give lower yields. In case of Example 12, where $NEt_3$ was used as base, undesired formation of appreciable amount of $C_{10}F_{21}H$ was observed.

Example 10

Perfluoroalkylation of 1,4-dibromobenzene

A mixture of 1,4-dibromobenzene (0.236 g, corresponding to 1 mmol 1,4-dibromobenzene), n-$C_{10}F_{21}$I (0.13 g, 0.2 mmol), DMSO (0.5 mL), (Sigma-aldrich 330159 with 5 wt % Pt, the wt % are based on the combined weight of Pt and C, with ca. 50 wt % water, the wt % based on the combined amount of Pt, C and water, 78 mg, 0.01 mmol, 5 mol % Pt based on n-$C_{10}F_{21}$I), and $Cs_2CO_3$ (65 mg, 0.2 mmol) were placed in a magnetically stirred Wheaton vial, the Wheatopn vial was placed in a well-plate in a Parr autoclave (Parr Instruments 4560 series). After replacing the air in the autoclave with nitrogen and increasing the pressure to 10 bars with nitrogen, the reaction mixture was stirred at 100° C. for 24 h. Then the reaction mixture was cooled, and then the pressure was released from the autoclave, and the solids were removed by filtration. Analysis of the product by $^{19}$F-NMR using the internal standard 1,4-difluorobenzene showed a conversion of 21% based on the perfluorodecyl iodide.

Examples 17 to 44 show the versatility of the method with different compounds ALKYLCOMPSUBST and FCLALKYLHALIDES, they were done in analogy to example 1, reaction conditions were 0.2 mmol of FCLALKYLHALIDE, CAT was Pt/C (Pt: 5 mol % relative to FCLALKYLHALIDE) and $Cs_2CO_3$ (1 molar equivalent based on FCLALKYLHALIDE). ALKYLCOMPSUBST was used in the amount of 0.5 mL in case of a ALKYLCOMPSUBST being liquid and 1 mmol in case of ALKYLCOMPSUBST being solid, reaction was done under $N_2$ atmosphere at 10 bar. Yield is isolated yield, in example 28 the yield was determined with $^{19}$F NMR with 1,4-difluorobenzene as an internal standard.

The reaction of example 44 was done with caffeine (1 mmol) in DMSO (0.5 mL) as SOL. The yield according to $^{19}$F-NMR with 1,4-difluorobenzene as an internal standard was 61%, isolated yield by pipette column using perfluorinated reverse phase silica gel was 49%.

Further details such as COMPSUBST, FCLALKYLHALIDE, ALKYLCOMPSUBST, T, t, yield and ratio of isomers of examples 17 to 44 are given in Tables 3 and 4.

TABLE 3

| Example | COMPSUBST | FCLALKYL-HALIDE | ALYKLCOMPSUBST |
|---|---|---|---|
| 17 | [benzene structure] | n-$F_{21}C_{10}$—I | [phenyl-$C_{10}F_{21}$ structure] |
| 18 | [1,4-dimethoxybenzene structure] | n-$F_{21}C_{10}$—I | [2,5-dimethoxyphenyl-$C_{10}F_{21}$ structure] |
| 19 | [1,4-dimethoxybenzene structure] | n-$F_{17}C_8$—I | [2,5-dimethoxyphenyl-$C_8F_{17}$ structure] |

TABLE 3-continued

| Example | COMPSUBST | FCLALKYL-HALIDE | ALYKLCOMPSUBST |
|---|---|---|---|
| 20 | 1,4-dimethoxybenzene | n-F₁₃C₆—I | 2-(C₆F₁₃)-1,4-dimethoxybenzene |
| 21 | 3,5-dimethoxyphenol | n-F₂₁C₁₀—I | 2-(C₁₀F₂₁)-3,5-dimethoxyphenol |
| 22 | 3,5-dimethoxyphenol | n-F₁₇C₈—I | 2-(C₈F₁₇)-3,5-dimethoxyphenol |
| 23 | 3,5-dimethoxyphenol | n-F₁₃C₆—I | 2-(C₆F₁₃)-1,3,5-trimethoxybenzene |
| 24 | 3,5-dimethoxyphenol | n-F₉C₄—I | 2-(C₄F₉)-1,3,5-trimethoxybenzene |
| 25 | naphthalene | n-F₂₁C₁₀—I | 1-(C₁₀F₂₁)naphthalene |
| 26 | naphthalene | n-F₁₇C₈—I | 1-(C₈F₁₇)naphthalene |

TABLE 3-continued

| Example | COMPSUBST | FCLALKYL-HALIDE | ALYKLCOMPSUBST |
|---------|-----------|-----------------|----------------|
| 27 | naphthalene | n-$F_9C_4$—I | 1-($C_4F_9$)-naphthalene |
| 29 | 1,3,5-trimethylbenzene | n-$F_{21}C_{10}$—I | 1,3,5-trimethyl-2-($C_{10}F_{21}$)-benzene |
| 30 | chlorobenzene | n-$F_{21}C_{10}$—I | 3-chloro-($C_{10}F_{21}$)-benzene |
| 31 | bromobenzene | n-$F_{21}C_{10}$—I | 3-bromo-($C_{10}F_{21}$)-benzene |
| 32 | 1,2-dimethoxybenzene | n-$F_{21}C_{10}$—I | 1,2-dimethoxy-($C_{10}F_{21}$)-benzene |
| 33 | 1-chloro-4-methoxybenzene | n-$F_{21}C_{10}$—I | 1-chloro-4-methoxy-($C_{10}F_{21}$)-benzene |
| 34 | 3′-methoxyacetophenone | n-$F_{21}C_{10}$—I | ($C_{10}F_{21}$)-substituted 3′-methoxyacetophenone |
| 35 | 3-methoxybenzaldehyde | n-$F_{21}C_{10}$—I | ($C_{10}F_{21}$)-substituted 3-methoxybenzaldehyde |

TABLE 3-continued

| Example | COMPSUBST | FCLALKYL-HALIDE | ALYKLCOMPSUBST |
|---|---|---|---|
| 36 | 3-methoxybenzonitrile | n-$F_{21}C_{10}$—I | 3-methoxy-4-($C_{10}F_{21}$)benzonitrile |
| 37 | 1-fluoro-3,5-dimethoxybenzene | n-$F_{21}C_{10}$—I | 1-fluoro-3,5-dimethoxy-($C_{10}F_{21}$)benzene |
| 38 | 2,5-dimethylthiophene | n-$F_{21}C_{10}$—I | 2,5-dimethyl-3-($C_{10}F_{21}$)thiophene |
| 39 | 2-bromothiophene | n-$F_{21}C_{10}$—I | 2-bromo-3-($C_{10}F_{21}$)thiophene |
| 40 | 1-methylpyrrole | n-$F_{21}C_{10}$—I | 1-methyl-2-($C_{10}F_{21}$)pyrrole |
| 41 | 1-methylpyrrole | n-$F_{13}C_{6}$—I | 1-methyl-2-($C_{6}F_{13}$)pyrrole |
| 42 | pyridine | n-$F_{21}C_{10}$—I | 2-($C_{10}F_{21}$)pyridine |
| 43 | 2,6-dimethylpyridine | n-$F_{21}C_{10}$—I | 2,6-dimethyl-3-($C_{10}F_{21}$)pyridine |
| 44 | caffeine | n-$F_{21}C_{10}$—I | 8-($C_{10}F_{21}$)caffeine |

TABLE 4

| Ex. | T [° C.] | t [h] | Yield in [%] (Ratio of Isomers in [%]) |
|---|---|---|---|
| 17 | 100 | 20 | 90 |
| 18 | 100 | 15 | 87 |
| 19 | 100 | 15 | 81 |
| 20 | 100 | 30 | 59 |
| 21 | 100 | 15 | 73 |
| 22 | 100 | 15 | 71 |
| 23 | 100 | 30 | 54 |
| 24 | 100 | 15 | 70 |
| 25 | 100 | 20 | 81 |
| 26 | 100 | 20 | 80 |
| 27 | 100 | 20 | 79 |
| 28 | 100 | 20 | 21 |

TABLE 4-continued

| Ex. | T [° C.] | t [h] | Yield in [%] (Ratio of Isomers in [%]) |
|---|---|---|---|
| 29 | 100 | 20 | 75 |
| 30 | 100 | 24 | 77 |
|    |     |    | (2-, 3-, 4- = 24, 39, 37) |
| 31 | 120 | 20 | 75 |
|    |     |    | (2, 3-, 4- = 18, 41, 41) |
| 32 | 120 | 20 | 81 |
|    |     |    | (2-, 4- = 11, 89) |
| 33 | 100 | 24 | 71 |
|    |     |    | (2-, 3- = 23, 77) |
| 34 | 100 | 24 | 77 |
|    |     |    | (2-, 4, 5-, 6- = 12, 54, 5, 29) |
| 35 | 100 | 24 | 73 |
|    |     |    | (2-, 4, 5-, 6- = 4, 80, 1, 15) |
| 36 | 120 | 20 | 69 |
|    |     |    | (2-, 4, 5-, 6- = 24, 24, 17, 35) |
| 37 | 100 | 20 | 78 |
|    |     |    | (2-, 4- = 62, 38) |
| 38 | 120 | 20 | 65 |
| 39 | 120 | 20 | 47 |
|    |     |    | (2-, 3, 4- = 81, 11, 8) |
| 40 | 50  | 20 | 94 |
| 41 | 50  | 30 | 68 |
| 42 | 100 | 20 | 65 |
|    |     |    | (2-, 3, 4- = 45, 46, 9) |
| 43 | 100 | 20 | 63 |
|    |     |    | (2-, 3- = 80, 20) |
| 44 | 100 | 20 | 49 |

Example 45

Perfluoralkylation of ethene-1,1-diyldibenzene

A mixture of 1,1-diphenylethylene (180 mg, 1 mmol), n-$C_{10}F_{21}$I (130 mg, 0.2 mmol), Pt/C (Sigma-aldrich 330159, with 5 wt % Pt, the wt % are based on the combined weight of Pt and C with ca. 50 wt % water, the wt % based on the combined amount of Pt, C and water, 78 mg, 0.01 mmol, 5 mol % Pt based on n-$C_{10}F_{21}$I), and $Cs_2CO_3$ (65 mg, 0.2 mmol) were placed in a Parr autoclave (25 mL capacity). After replacing the air in the autoclave with nitrogen and increasing the pressure to 10 bars with nitrogen, the reaction mixture was stirred at 100° C. for 20 h. Then the reaction mixture was cooled, and then the pressure was released from the autoclave. The solids were removed by filtration. The filtrate was extracted 4 times with $CH_2Cl_2$. The combined organic phase dried with $MgSO_4$, filtered, and concentrated under vacuum. The crude product was purified by column chromatography on silica gel to give 119 mg fluorinated product. The major product is the (3,3,4,4,5,5,6,6,7,7,8,8,9,9,10,10,11,11,12,12,12-henicosafluorododec-1-ene-1,1-diyl)dibenzene. The identity of the product was confirmed using HRMS EI (m/z): [M]+ calculated for $C_{24}H_{11}F_{21}$, 698.051999. found, 698.05131. The minor product is (3,3,4,4,5,5,6,6,7,7,8,8,9,9,10,10,11,11,12,12,12-henicosafluorododecane-1,1-diyl)dibenzene. The identity of the product was confirmed using HRMS EI (m/z): [M]+ calculated for $C_{24}H_{13}F_{21}$, 700.06764. found, 700.06668. The position of $C_{10}F_{21}$ was determined by NMR of the major product. $^1$H NMR (300 MHz, $CDCl_3$) delta=7.44 to 7.26 (m, 10H), 6.14 (t, J=14.7, 1H). $^{19}$F NMR (282 MHz, $CDCl_3$) delta=−80.33 (3F), −103.13 (2F), −120.90 to −122.59 (14F), −125.79 (2F).

Example 46

Perfluoralkylation of 3,3-dimethylbut-1-ene

A mixture of 3,3-dimethylbut-1-ene (374 mg, 3.39 mmol), n-$C_{10}F_{21}$I (130 mg, 0.2 mmol), Pt/C (Sigma-aldrich 330159, with 5 wt % Pt, the wt % are based on the combined weight of Pt and C with ca. 50 wt % water, the wt % based on the combined amount of Pt, C and water, 78 mg, 0.01 mmol, 5 mol % Pt based on n-$C_{10}F_{21}$I), and $Cs_2CO_3$ (65 mg, 2 mmol) were placed in a magnetically stirred Wheaton vial, the Wheaton vial was placed in a Parr autoclave (Parr Instruments 4560 series). After replacing the air in the autoclave with nitrogen and increasing the pressure to 10 bars with nitrogen, the reaction mixture was stirred at 60° C. for 20 h. Then the reaction mixture was cooled, and then the pressure was released from the autoclave. The solids were removed by filtration. The filtrate was extracted 4 times with $CH_2Cl_2$. The combined organic phase dried with $MgSO_4$, filtered, and concentrated under vacuum to give 102 mg fluorinated mixture (determined by $^{19}$F NMR). The major identified product is 5,5,6,6,7,7,8,8,9,9,10,10,11,11,12,12,13,13,14,14,14-henicosafluoro-2,2-dimethyltetradec-3-ene. The identity of the product was confirmed using HRMS EI (m/z): [M]+ calculated for $C_{16}H_{11}F_{21}$, 602.05199. found, 602.05105.

Example 47

Perfluoralkylation of 1-octyne

A mixture of 1-octyne (327 mg, 3.88 mmol), n-$C_{10}F_{21}$I (130 mg, 0.2 mmol), Pt/C (Sigma-aldrich 330159, with 5 wt % Pt, the wt % are based on the combined weight of Pt and C with ca. 50 wt % water, the wt % based on the combined amount of Pt, C and water, 78 mg, 0.01 mmol, 5 mol % Pt based on n-$C_{10}F_{21}$I), and $Cs_2CO_3$ (65 mg, 2 mmol) were placed in a magnetically stirred Wheaton vial, the Wheaton vial was placed in a Parr autoclave (Parr Instruments 4560 series). After replacing the air in the autoclave with nitrogen and increasing the pressure to 10 bars with nitrogen, the reaction mixture was stirred at 60° C. for 20 h. Then the reaction mixture was cooled, and then the pressure was released from the autoclave. The solids were removed by filtration. The filtrate was extracted 4 times with $CH_2Cl_2$. The combined organic phase dried with $MgSO_4$, filtered, and concentrated under vacuum to give 111 mg fluorinated product. The identity of the product was confirmed using NMR. $^1$H NMR (300 MHz, $CDCl_3$) delta=2.61 to 2.51 (m, 2H), 1.89 to 1.42 (m, 2H), 1.23 (s, 6H), 0.82 (t, J=6.5, 3H). $^{19}$F NMR (282 MHz, $CDCl_3$) delta=−80.65 (3F), −105.04 (2F), −121.16 to −123.01 (14F), −125.93 (2F).

The invention claimed is:
1. A method for the preparation of a fluoro, chloro or fluorochloro alkylated compound by a reaction of a compound COMPSUBST with a compound FCLALKYLHALIDE with heterogeneous catalysis using a catalyst CAT in the presence of a compound CAESCARB; wherein
   FCLALKYLHALIDE is a compound of formula (III);

$$R3-X \qquad (III)$$

X is Cl, Br or I;
R3 is $C_{1-20}$ alkyl or a $C_{1-20}$ alkyl wherein in the alkyl chain at least one hydrogen is substituted by F or Cl;
CAESCARB is $Cs_2CO_3$, $CsHCO_3$ or a mixture thereof;
CAT is Pt/C;
COMPSUBST is selected from the group consisting of a compound COMPSUBST-I, ethene, propene, ethine, and polystyrene;
COMPSUBST-I is a ring RINGA;
RINGA is a 5 or 6 membered carbocyclic or heterocyclic aromatic ring, when RINGA is a heterocyclic ring, then RINGA has 1, 2 or 3 identical or different endocyclic heteroatoms independently from each other selected from the group consisting of N, O and S, when RINGA is a 5 membered ring, then RINGA is unsubstituted or substituted by 1, 2, 3 or 4 identical or different substituents, when RINGA is a 6 membered ring then RINGA is unsubstituted or substituted by 1, 2, 3, 4 or 5 identical or different substituents, any of said substituents of RINGA is independently from any other of said substituent of RINGA selected from the group consisting of $C_{1-10}$ alkyl, $C_{3-8}$ cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, $S(O)_2$R50, CH=C(H)R28,

C≡C—R24, benzyl, phenyl and naphthyl;

RINGA can be condensed with a ring RINGB, RINGB is a 5 or 6 membered carboryclic or heterocyclic ring, when RINGB is a heterocyclic ring, is contains 1, 2 or 3 identical or different endocyclic heteroatoms independently from each other selected from the group consisting of N, O and S;

RINGB is unsubstituted or substituted with 1, 2 or 3 in case of RINGB being a 5 membered ring, with 1, 2, 3 or 4 in case of RINGB being a 6 membered ring, identical or different substituents independently from each other selected from the group consisting of $C_{1-10}$ alkyl, $C_{3-8}$ cycloalkyl, $C_{1-4}$ alkoxy, OH, N(R17)R18, CN, NH—OH, NO, $NO_2$, F, Cl, Br, I, $CF_3$, $(CH_2)_n$—C(O)Y2, $S(O)_2$R51, CH=C(H)R38,

C≡C—R34, benzyl, phenyl and naphthyl;

any of said $C_{1-10}$ alkyl substitutent of RINGA or RINGB is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;

any of said benzyl, phenyl and naphthyl substituent of RINGA or RINGB is independently from each other unsubstituted or substituted with 1, 2, 3, 4 or 5 identical or different substituents selected from the group consisting of halogen, $C_{1-4}$ alkoxy, $NO_2$ and CN;

m, n and q are identical or different and independently from each other 0, 1, 2, 3, 4, 5, 6, 7, 8, 9 or 10;

Y1, Y2 and R13 are identical or different and independently from each other selected from the group consisting of H, OH, C(R14)(R15)R16, $C_{2-6}$ alkyl, O—$C_{1-6}$ alkyl, phenyl, benzyl, O-phenyl, O—$C_{1-6}$ alkylen-O—$C_{1-6}$ alkyl and N(R19)R20;

R14, R15 and R16 are identical or different and independently from each other selected from the group consisting of H, F, Cl and Br;

R10, R11, R17, R18, R19 and R20 are identical or different and are independently from each other H or $C_{1-6}$ alkyl, or R10 and R11, R17 and R18 or R19 and R20 represent together a tetramethylene or a pentamethylene chain;

R50 and R51 are identical or different and independently from each other selected from the group consisting of OH, $C_{1-6}$ alkyl and $C_{1-6}$ alkoxy;

R24, R34, R28 and R38 are identical or different and independently from each other selected from the group consisting of H, $C_{1-10}$ alkyl, C(R25)(R26)—O—R27;

R25, R26 and R27 are identical or different and independently from each other selected from the group consisting of H and $C_{1-10}$ alkyl.

2. The method according to claim 1, wherein

COMPSUBST is selected from the group consisting of compound COMPSUBST-I and polystyrene;

wherein COMPSUBST-I is selected from the group consisting of

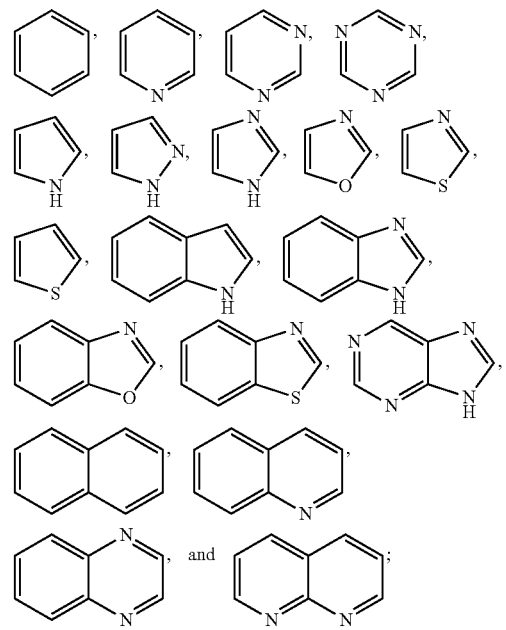

wherein COMPSUBST-I is unsubstituted or substituted by 1, 2, 3 or 4 in case of COMPSUBST-I being a monocyclic compound with 5 endocyclic atoms, by 1, 2, 3, 4 or 5 in case of COMPSUBST-I being a monocyclic compound with 6 endocyclic atoms, by 1, 2, 3, 4, 5 or 6 in case of COMPSUBST-I being a bicyclic compound wherein a 5-membered and a 6-membered ring are ortho-fused, by 1, 2, 3, 4, 5, 6 or 7 in case of COMPSUBST-I being a bicyclic compound wherein two 6-membered rings are ortho-fused, identical or different substituents independently from each other selected from the group consisting of $C_{1-10}$ alkyl, $C_{3-8}$ cycloalkyl, $C_{1-4}$ alkoxy, OH, C(H)=O, N(R10)R11, CN, NH—OH, NO, $NO_2$, F, Cl, Br, I, $CF_3$, $(CH_2)_m$—C(O)Y1, $S(O)_2$R50, CH=C(H)R28,

C≡C—R24, benzyl, phenyl and naphthyl, said $C_{1-10}$ alkyl substitutent of COMPSUBST-I is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, S($O_2$)—$C_{1-10}$ alkyl, O—$C_{1-6}$ alkylen-O—$C_{1-6}$ alkyl, $C_{3-8}$ cycloalkyl and 1,2,4-triazolyl;

said benzyl, phenyl and naphthyl substitutent of COMPSUBST-I is independently from each other unsubstituted or substituted with 1, 2, 3, 4 or 5 identical or different substituents selected from the group consisting of halogen, $C_{1-4}$ alkoxy, $NO_2$ and CN.

3. The method according to claim 1, wherein m, n and q are identical or different and independently from each other 0, 1, 2, 3 or 4.

4. The method according to claim 1, wherein

COMPSUBST is selected from the group consisting of benzene, pyrazole,

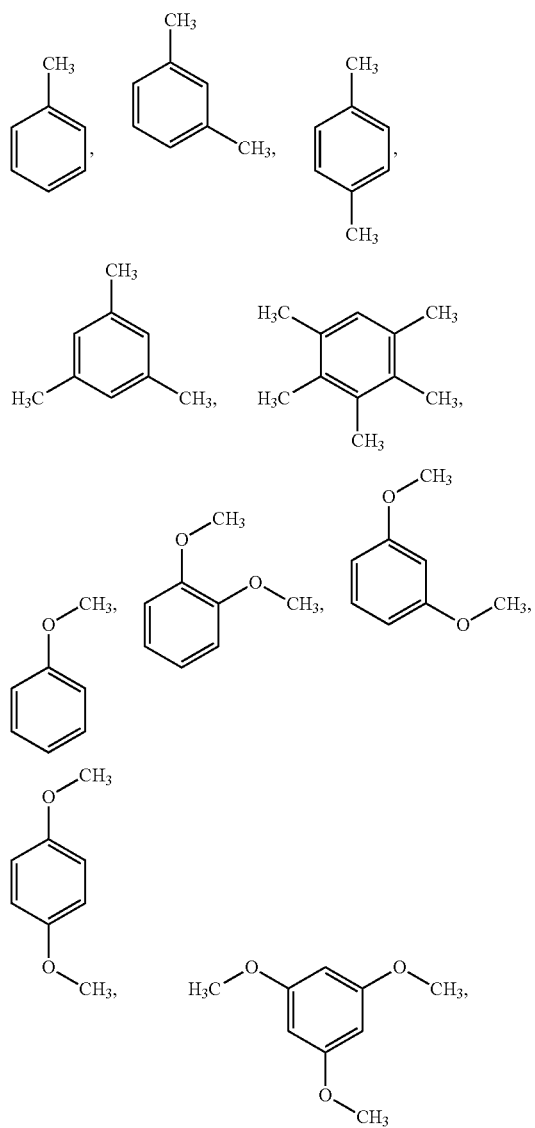

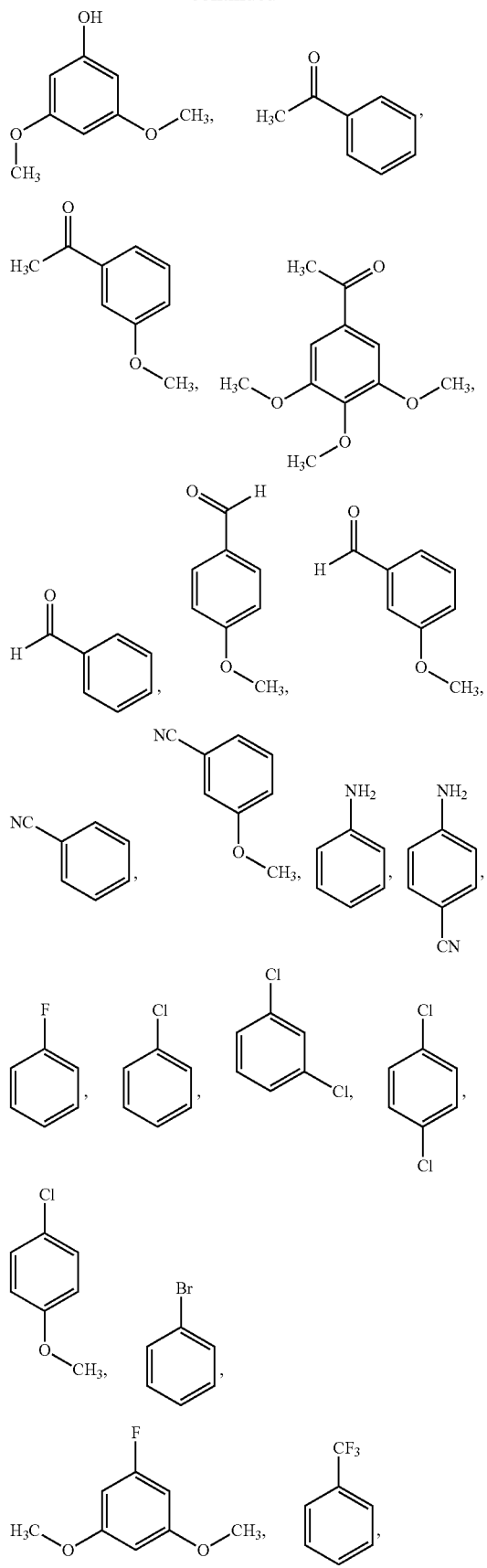

-continued

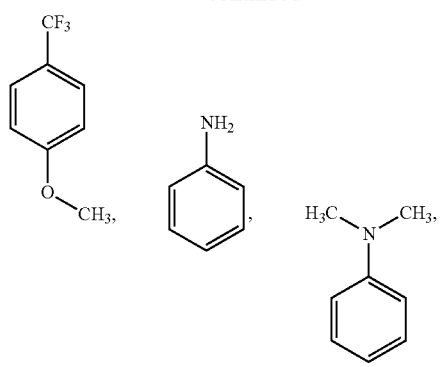

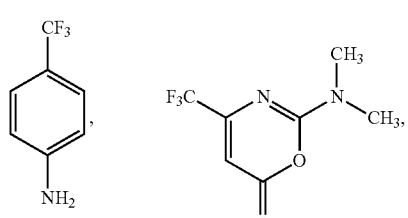

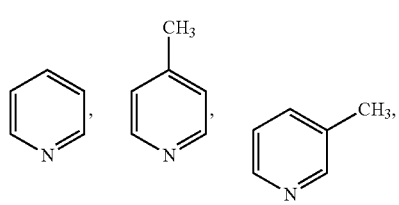

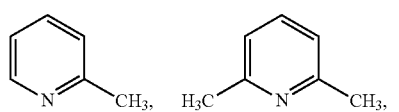

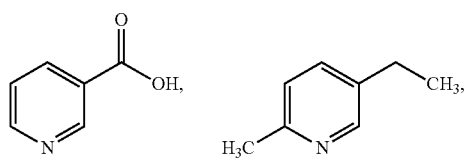

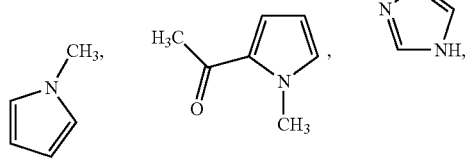

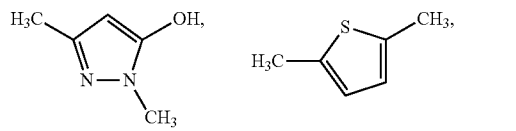

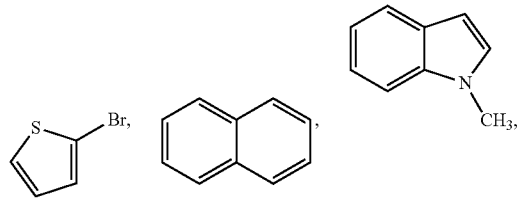

-continued

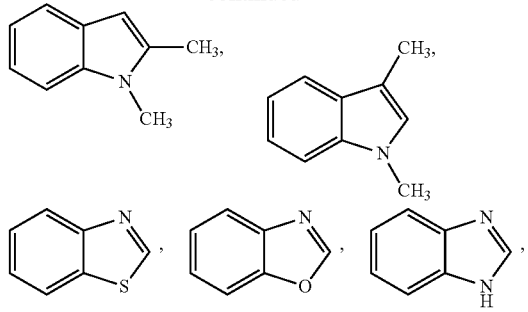

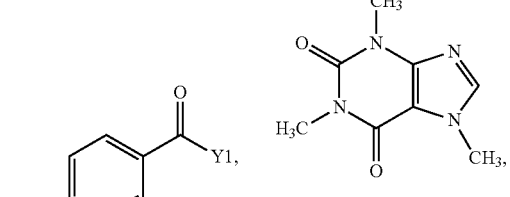

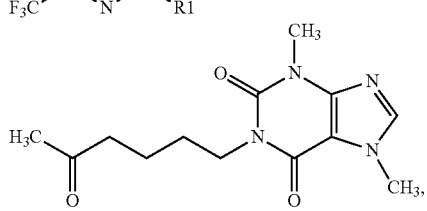

and
polystyreneR44 is selected from the group consisting of C.

5. The method according to claim 1, wherein
X is Br or I.

6. The method according to claim 1, wherein
X is I.

7. The method according to claim 1, wherein
compound FCLALKYLHADLIDE is a perfluoroalkyl halide, $F_2HC$—Cl or $F_2HC$—Br.

8. The method according to claim 1, wherein
X is Cl, Br or I, and
R3 is perfluoro $C_{1-20}$ alkyl; or
FCLALKYLHADLIDE is $F_2HC$—Cl or $F_2HC$—Br.

9. The method according to claim 1, wherein
FCLALKYLHALIDE is selected from the group consisting of $F_{21}C_{10}$—I, $F_{17}C_8$—I, $F_{13}C_6$—I, $F_9C_4$—I, $F_3C$—I, $F_3C$—Br, $F_3C$—Cl, $F_2HC$—Cl and $F_2HC$—Br.

10. The method according to claim 1, wherein
the reaction is done in the presence of a compound COMPSALT;
wherein COMPSALT is selected from the group consisting of NaI, KI, CsI and N(R30)(R31)(R32)R33I; and
R30, R31, R32 and R33 are identical or different and independently from each other selected from the group consisting of H and $C_{1-10}$ alkyl.

11. The method according to claim 10, wherein
R30, R31, R32 and R33 are identical or different and independently from each other selected from the group consisting of H and $C_{2-6}$ alkyl.

12. The method according to claim 10, wherein
COMPSALT is selected from the group consisting of NaI and (n-Bu)$_4$NI.

13. The method according to claim 1, wherein
the amount of Pt in CAT is from 0.1 to 20%, the % are % by weight and are based on the combined weight of Pt and C in CAT.

14. The method according to claim 1, wherein from 0.001 to 20% of Pt are used in the reaction, the % are % by weight % and are based on the weight of FCLALKYLHALIDE.

15. The method according to claim 1, wherein from 1 to 20 mol equivalents of COMPSUBST are used in the reaction, the mol equivalents are based on the molar amount of FCLALKYLHALIDE.

16. The method according to claim 1, wherein from 0.1 to 10 mol equivalents of CAESCARB are used in the reaction, the mol equivalents are based on the molar amount of FCLALKYLHALIDE.

* * * * *